United States Patent [19]

Sturm et al.

[11] 3,941,579
[45] Mar. 2, 1976

[54] REGULATING THE GROWTH OF PLANTS AND CONTROLLING WEEDS WITH CARBONYL-SUBSTITUTED AZABICYCLOALKANES

[75] Inventors: Elmar Sturm, Arlesheim; Hans Joerg Cellarius, Riehen; Christian Vogel, Binningen, all of Switzerland

[73] Assignee: Ciba-Geigy Corporation, Ardsley, N.Y.

[22] Filed: Sept. 10, 1973

[21] Appl. No.: 395,885

Related U.S. Application Data

[62] Division of Ser. No. 216,778, Jan. 10, 1972, Pat. No. 3,776,912.

[30] Foreign Application Priority Data

Jan. 14, 1971 Switzerland.......................... 553/71

[52] U.S. Cl. ............................ 71/94; 71/66; 71/67; 71/76; 71/95
[51] Int. Cl.²........................................... A01N 9/22
[58] Field of Search................................. 71/94, 95

[56] References Cited
UNITED STATES PATENTS

| | | | |
|---|---|---|---|
| 3,066,020 | 11/1962 | Tilles et al. ............................ | 71/94 |
| 3,318,676 | 5/1967 | Harman et al. ......................... | 71/94 |
| 3,330,643 | 7/1967 | Harman et al. ......................... | 71/94 |
| 3,639,404 | 2/1972 | Richter et al. .......................... | 71/94 |
| 3,661,916 | 5/1972 | Sturm et al. ............................ | 71/94 |
| 3,705,165 | 12/1972 | Sturm et al. ............................ | 71/94 |

*Primary Examiner*—Glennon H. Hollrah
*Attorney, Agent, or Firm*—Frederick H. Rabin

[57] ABSTRACT

Substituted azabicycloalkanes of the formula I

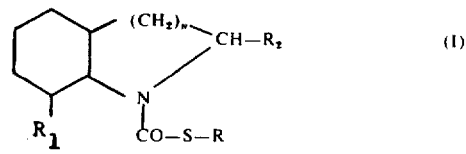

wherein R represents an alkyl radical which contains 2 or 3 carbon atoms and is substituted by chlorine or a straight-chain or branched alkenyl radical containing 3 or 4 carbon atoms, $R_1$ and $R_2$ represent hydrogen or the one represents methyl and the other represents hydrogen, and $n$ is the number 1 or 2, may be used for influencing the growth of plants, preferably for combating weeds in rice-cultures.

11 Claims, No Drawings

REGULATING THE GROWTH OF PLANTS AND CONTROLLING WEEDS WITH CARBONYL-SUBSTITUTED AZABICYCLOALKANES

This is a division of application Ser. No. 216,778, filed on Jan. 10, 1972, now U.S. Pat. No. 3,776,912.

The present invention relates to substituted azabicycloalkanes, process for their manufacture, also to selective herbicidal agents which contain such substituted azabicycloalkanes as active substances, and to processes for combating grass-like weeds wherein the new active substances are used or the agents that contain them.

The term "azabicycloalkanes" is used here and hereinafter to denote substituted 2-azabicyclo[4.4.0]-decanes (decahydroquinolines) and 7-azabicyclo[4.3.0]-nonanes (octahydroindoles).

The substituted azabicycloalkanes according to the invention correspond to the formula I:

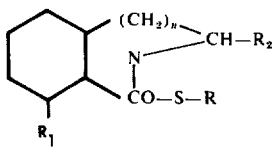

wherein R represents an alkyl radical which contains 2 or 3 carbon atoms and is substituted by chlorine or a straight-chain or branched alkenyl radical containing 3 or 4 carbon atoms, $R_1$ and $R_2$ each represent hydrogen or the one represents methyl and the other represents hydrogen, and n is the number 1 or 2.

By an alkyl radical which contains 2 to 3 carbon atoms and is substituted by chlorine is to be understood the mono-substituted ethyl, n-propyl or isopropyl radical.

The straight-chain or branched alkenyl radicals containing 3 to 4 carbon atoms include the allyl, 2-butenyl, 3-butenyl and the methylallyl radical.

The substituted azabicycloalkanes of the formula I are obtained according to the invention by reacting an azabicycloalkane of the formula II

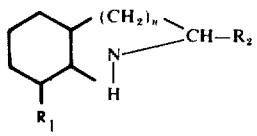

either with a thiocarbonic acid halide of the formula III

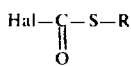

or with the constituent components of such a thiocarbonic acid halide, namely phosgene and an alkali metal salt of a mercaptan of the formula IV $$R - SH \qquad (IV)$$

in the presence of an acid binding agent. In the formulae II to IV, R, $R_1$, $R_2$ and n have the meanings assigned to them under formula I and Hal in the formula III represents chlorine or bromine. It is advisable to carry out the reactions in a solvent or diluent which is inert towards the reaction components. The nature of the solvent to be used is very largely determined by the acid binding agent used in the reaction. If organic bases, such as tertiary amines, are used, it is advisable to use organic solvents also. In the case of inorganic bases, water and aqueous mixtures of organic solvents which are miscible with water are suitable. In general, the following tertiary amines may be used as acid binding agents: pyridine and pyridine bases, triethylamine etc. The respective azabicycloalkane of the formula II, used in excess in the reaction, may likewise be used as acid binding agent. Suitable inorganic bases are the hydroxides and carbonates of alkali and alkaline earth metals, chiefly sodium hydroxide, sodium carbonate, potassium carbonate, also the hydroxides and carbonates of lithium, barium, strontium, magnesium, as well as quaternary ammonium compounds which react as bases in the presence of water, for example tetramethylammonium hydroxide etc.

As solvents there may be used: aliphatic and aromatic hydrocarbons and halogenated hydrocarbons, such as benzene, toluene, xylenes, petroleum ether, chlorobenzene, methylene chloride, chloroform, carbon tetrachloride, ether and ether-like solvents such as dialkyl ether, tetrahydrofuran. Suitable solvents which are miscible with water are alkanols, ketones etc.

In the reaction of an azabicycloalkane of the formula II with phosgene and an alkali metal salt of a mercaptan of the formula IV the azabicycloalkane-2-carboxylic acid halide obtained as intermediate product can be reacted without further purification with the salt of the mercaptan.

According to a further process of the present invention the new substituted azabicycloalkanes of the formula II are obtained by reacting an azabicycloalkane of the formula II, in the presence of an acid binding agent, with carbon oxysulfide and subsequently with a chloroalkylating agent or an alkenylating agent. Suitable acid binding reagents are those cited above, preferably the alkali metal hydroxides. Suitable chloroalkylating agents are primarily chloroalkyl halides.

The reactions according to the invention of a substituted azabicycloalkane of the formula II according to one of the indicated methods to give compounds of the formula I are carried out at temperatures of −20°C to +100°C, preferably between 0°C and +30°C.

Some of the azabicycloalkanes of the formula II are known and some are new compounds. The new compounds are manufactured in known manner by hydrogenating the corresponding aromatic heterocycles at 100°–180°C and 100–200 gauge pressure, in aqueous emulsion and in the presence of noble metal catalysts, for example ruthenium/carbon catalysts.

The starting compounds comprised by the formula II are present in 2 isomeric forms: in the cis- and in the trans-configuration. In the case of the 2-azabicyclo[4.4.0]decane (decahydroquinoline), with $R_1$ and $R_2$ representing hydrogen in the formula II, the cis- and trans-isomers are easily isolated and lead to 2 series of compounds of the formula I with cis- and trans-configuration.

The new substituted azabicycloalkanes of the formula I possess excellent herbicidal properties and are suitable partly as general herbicides and partly for combating weeds and grass-like weeds in rice cultures (water and dry rice cultures). Varieties of weeds which are difficult to combat in rice cultures are attacked and destroyed by the compounds of the formula I. Examples of such weeds in water rice cultures are: Echinochloa sp., Eleocharis sp., Monochoria, Sagittaria, Panicum sp., Cyperaceen, Rotala, Lindernia, Vandellia, Paspalum sp., etc.; and in dry rice cultures likewise Echinochloa sp., Digitaria sp., Brachiaria sp., Sida sp., cyperaceen, Acanthosperum sp. etc. Since the active substances gradually destroy the undesirable plants and thus do not have any excessively deleterious effect on the oxygen balance and on the balance of nature, they are very well suited for application in water rice cultures. Moreover, the active substances possess a broad activity spectrum against various water weeds, for example against emersed plants, aquatic plants with and without floating leaves, submersed plants, algae etc.

Both the cis- and the trans-azabicycloalkanes of the formula I as well as mixtures of both forms are herbicidally active.

The broad activity spectrum of the new substituted azabicycloalkanes of the formula I also makes it possible to use them in the important task of combating weeds and grass-like weeds in the area surrounding the rice cultures, for example ditches, canal beds, dams etc. Not only the cited grass-like weeds occurring in rice cultures but also other grass-like and broad-leaved weeds are destroyed by these active substances. The active substances may be used for destroying a crop of weeds which has already sprouted when preparing the rice beds and after the crop plants have emerged. Both rice which is planted in water and that which is planted dry do not suffer any damage when the new substituted azabicycloalkanes are applied in the conventional concentrations and damage which is very largely reversible when high rates of application are used. The rates of application vary and depend on the time of application; they are between 0.5 and 6 kg of active substance per hectare, preferably 4 kg per hectare, in the case of application before the plants have germinated. Rates of application of 10–30 kg of active substance per hectare are used to totally destroy the entire crops of weeds, for example on the fallow land neighbouring on the cultivated areas and to determine the general herbicidal activity. The crop rotation important for the rice culture may proceed on application of the new active substances without any detrimental effects.

The azabicycloalkanes of the formula I may also be used furthermore as growth regulators, for example for defoliating, delaying blossoming etc. The new compounds influence the vegetative plant growth and germination power and promote fruit development and the evolution of abscission tissues. The development of side shoots in various species of plants is very substantially diminished. The new compounds also have a promotor action, for example the latex flow in Hevea brasiliensis is promoted. As experiments have shown, the rooting of seedlings and cuttings are also the tuber formation in potatoes are favourably influenced. The germination power of seeds, for example of seed potatoes and legumes, is promoted on the use of low and prevented on the use of high concentrations.

Both effects are of economic importance. In the case of many ornamental and useful plants it is possible to control the term of blossoming and the number of blossoms. If all shrubs blossom simultaneously, they can be harvested within a comparatively short time.

Experiments also showed that a thinning out of blossom and fruit occurred in fruit trees. Furthermore, the ripening and colouring of fruit, for example in the case of apples, peaches, tomatoes, bananas and pineapples, were accelerated and improved. The abscission of fruit and leaves is greatly facilitated by the formation of abscission tissue — a factor which is of great economic importance in the mechanical harvesting of, for example, citrus fruit or cotton.

Substituted azabicycloalkanes of the formula I have hitherto not been described. Herbicidal azabicyclo[3.2.2]-nonanes and polymethyleneimino-thiocarbamates are described in U.S. Pat. Nos. 3,344,134 and 3,198,786, respectively, but their action on grass-like weeds with good selectivity in rice is slight and dicotyledonous weeds are not damaged. With comparable selectivity towards rice, the active substances according to the invention of the formula I have a much better action against grass-like weeds and a broad activity spectrum towards dicotyledonous weeds. Even when used in very low rates of application, some are herbicidally active against numerous grass-like weeds against which the cited comparative compounds show no activity, and they are well tolerated by cereals, especially maize and wheat, also soya and cotton.

The herbicidal agents are manufactured by mixing the active substances with suitable carriers and/or dispersing agents. In order to broaden the activity spectrum it is possible to add to these agents still other herbicides, for example from the series of the triazines, such as halogeno-diamino-s-triazines, alkoxy- and alkylthio-diamino-s-triazines, triazoles, diazines, such as uraciles, aliphatic carboxylic acids and halogenocarboxylic acids, halogenated benzoic acids and phenylacetic acids, aryloxyalkanecarboxylic acids, hydrazides, amides, nitriles, esters of such carboxylic acids, carbamic acids and thiocarbamic acids, phenyl ureas etc.

The following Examples illustrate the process for the manufacture of the azabicycloalkane derivatives of the formula I.

EXAMPLE 1

Beneath a solution of 20 g of trans-decahydroquinoline in 100 ml of benzene is introduced a layer consisting of a solution of 5.8 g of sodium hydroxide in 100 ml of water. While stiring vigorously and cooling to 5°–10°C, 20 g of chlorothioformic acid allyl ester are then added dropwise to the mixture. Upon completion of the reaction, stirring is continued for 3 hours, the phases are separated, the benzene phase is washed until neutral, dried, and the benzene evaporated in vacuo. The residual oil is distilled in vacuo to yield 24 g (70% of theory) of 1-(allylthiocarbonyl)-trans-decahydroquinoline (b.p. 110°–116°C/0.2 Torr).

EXAMPLE 2

Beneath a solution of 13.9 g of cis-decahydroquinoline in 200 ml of diethyl ether is introduced a layer consisting of an aqueous solution of 4 g of sodium hydroxide. While stirring vigorously and cooling to 0°–5°C, 9.8 g of phosgene is passed into this mixture. When the mixture shows a neutral reaction, the ether phase is separated and added dropwise to a suspension of 13 g of sodium-(3-chloro-propyl)-mercaptide in absolute ether. The batch is left to stand for 24 hours and then the resulting precipitate is collected by suction filtration. The ether is evaporated off and the residual oil so obtained is distilled in vacuo to yield 19 g (68% of theory) of 1-(3-n-chloro-propylthiocarbonyl)-cis-decahydroquinoline (b.p. 140°–142°C/0.01 Torr).

EXAMPLE 3

To a suspension of 13.9 g of trans-decahydroquinoline in 200 ml of water are added 4.0 g of sodium hydroxide and, while stirring slowly, 8.0 g of carbon oxysulphide are passed into the mixture at 0°–5°C over the course of 1 hour. After a further quarter of an hour 23 g of 1,3-bromochloropropane are added all at once and the batch is stirred for 20 hours at 20°C. The precipitated oil is taken up in ether, the ether solution shaken out with dilute hydrochloric acid, washed with water, dried and evaporated in vacuo. The resulting oil is distilled in vacuo. 10.6 Grams (38% of theory) of 1-(3-n-chloropropylthiocarbonyl)-trans-decahydroquinoline are obtained in the form of a colorless oil (b.p. 130°–138°C/0.01 Torr).

The compounds of the formula I listed in Table 1 are manufactured according to the methods described in these Examples by using corresponding amounts of azabicycloalkane and thiocarbonic acid halide of the formula III or carbon oxysulphide and alkylating (or alkenylating) agent:

The herbicidal action of the new compounds is illustrated by the following tests.

Selective Pre-emergence Test with sown Test Plants

Immediately after sowing the test plants in seed dishes the active substances, in the form of an aqueous suspension (obtained from a 25% wettable powder), are applied to the surface of the soil. The seed dishes are then kept in day-light at 22°–25°C and 50–70% relative atmospheric humidity.

Evaluation takes place 28 days according to the following key:

9 = plants undamaged = control
1 = plants died off
8–2 = intermediate stages of damage The following test plants were sown:

| | |
|---|---|
| rice (dry) | (*Oryza*) |
| rice (in water) | |
| wheat | (*Triticum vulgare*) |
| soya | (*Glycine hispida*) |
| cotton | (*Gossypium*) |
| maize | (*Zea mais*) |
| ray grass | (*Lolium multiflorum*) |
| Italian millet | (*Setaria italica*) |
| panicum grass | (*Echinochloa crus galli*) |
| a) dry | |
| b) in water | |
| rough meadow grass | (*Poa trivialis*) |
| foxtail grass | (*Alopecurus myosuroides*) |
| crabgrass | (*Digitaria sanguinalis*) |

Table 1

| Example No. | Compound | Boiling Point |
|---|---|---|
| 4 | 1-(allylthio-carbonyl)-cis-decahydroquinoline | 106–110°/0.05 Torr |
| 5 | 1-(allylthio-carbonyl)-2-methyl-decahydroquinoline | 123–124°/0.01 Torr |
| 6 | 1-(2-chloroethylthio-carbonyl)-trans-decahydroquinoline | 140°/0.1 Torr |
| 7 | 1-(2-chloroethylthio-carbonyl)-cis-decahydroquinoline | 138°/0.08 Torr |
| 8 | 1-(2-butenylthio-carbonyl)-cis-decahydroquinoline | 139–140°/0.15 Torr |
| 9 | 1-(2-chloroethylthio-carbonyl)-8-methyl-decahydroquinoline | 150–152°/0.1 Torr |
| 10 | 1-(3-n-chloropropylthio-carbonyl)-octahydroindole | 142–145°/0.09 Torr |
| 11 | 1-(allylthio-carbonyl)-octahydroindole | 145–155°/0.04 Torr |
| 12 | 1-(3-n-chloropropylthio-carbonyl)-2-methyl-octahydroindole | 145–150°/0.1 Torr |

Table II

Condition of the sown plants after 4 weeks

| Active substance Example No. | Conc. kg/ha | Rice dry | Rice in water | Crop Plants wheat | Soya | Cotton | Maize | Weeds Lolium multifl. | Setaria ital. | Echinochloa crus galli dry | Echinochloa crus galli in water | Poa triv. | Alopecurus myos. | Digitaria sanguin. |
|---|---|---|---|---|---|---|---|---|---|---|---|---|---|---|
| | 8 | 9 | 8 | 8 | 9 | 9 | 9 | 2 | 2 | 1 | 1 | 1 | 2 | 1 |
| | 4 | 9 | 8 | 9 | 9 | 9 | 9 | 3 | 2 | 1 | 2 | 1 | 2 | 1 |
| 1 | 2 | 9 | 9 | 9 | 9 | 9 | 9 | 8 | 2 | 2 | 2 | 2 | 9 | 1 |
| | 1 | 9 | 9 | 9 | 9 | 9 | 9 | 9 | 4 | 2 | 6 | 9 | 9 | 2 |
| | 8 | 9 | 7 | 8 | 7 | 8 | 8 | 1 | 1 | 1 | 1 | 1 | 1 | 1 |
| | 4 | 9 | 8 | 8 | 7 | 9 | 8 | 2 | 1 | 1 | 1 | 1 | 2 | 1 |
| 2 | 2 | 9 | 9 | 9 | 9 | 9 | 8 | 7 | 1 | 2 | 2 | 1 | 2 | 1 |
| | 1 | 9 | 9 | 9 | 9 | 9 | 9 | 9 | 2 | 2 | 2 | 1 | 7 | 2 |
| | 8 | — | — | 8 | 9 | 9 | 9 | 3 | 2 | 1 | 1 | 2 | 2 | 2 |
| | 4 | — | — | 9 | 9 | 9 | 9 | 3 | 2 | 1 | 2 | 2 | 2 | 2 |
| 3 | 2 | 8 | 8 | 9 | 9 | 9 | 9 | 3 | 2 | 2 | 3 | 2 | 2 | 3 |
| | 1 | 9 | 9 | 9 | 9 | 9 | 9 | 7 | 4 | 5 | 9 | 4 | 4 | 4 |
| | 8 | — | — | — | 7 | 7 | 7 | 1 | 1 | 1 | 1 | 1 | 1 | 1 |
| | 4 | — | — | — | 8 | 8 | 7 | 1 | 1 | 2 | 1 | 1 | 2 | 1 |
| 4 | 2 | 8 | 8 | — | 9 | 9 | 8 | 2 | 1 | 3 | 2 | 1 | 2 | 1 |
| | 1 | 9 | 9 | — | 9 | 9 | 9 | 6 | 1 | 5 | 4 | 2 | 6 | 1 |

Table II-continued

Condition of the sown plants after 4 weeks

| Active substance Example No. | Conc. kg/ha | Rice dry | Rice in water | Crop Plants wheat | Crop Plants Soya | Crop Plants Cotton | Crop Plants Maize | Weeds Lolium multifl. | Weeds Setaria ital. | Echinochloa crus galli dry | Echinochloa crus galli in water | Poa triv. | Alopecurus myos. | Digitaria sanguin. |
| --- | --- | --- | --- | --- | --- | --- | --- | --- | --- | --- | --- | --- | --- | --- |
|   | 4 | 9 | 9 | 9 | 9 | 9 | — | 3 | 3 | 3 | 1 | 4 | 6 | 2 |
| A | 2 | 9 | 9 | 9 | 9 | 9 | — | 9 | 4 | 6 | 7 | 8 | 6 | 3 |
|   | 1 | 9 | 9 | 9 | 9 | 9 | — | 9 | 9 | 7 | 9 | 9 | 9 | 9 |

A = 3-(ethylthio-carbonyl)-3-azabicyclo[3.2.2.]nonane, known from U.S. Pat. No. 3,344,134

The following tests illustrate the influence on the vegetative storage system of various species of plants:

II. Inhibition of the growth in height a. Application to grasses

A mixture of grasses, consisting of *Lolium perenne* (20%), *Poa pratensis* (23%), *Festuca ovin* (10%) and *Festuca rubra* (47%), is cultivated for 4 months in seed dishes and cut once weekly. The freshly cut grass, approx. 1.5 cm high, is then treated with aqueous or aqueous-acetonic active substance solutions. Subsequently the grass is kept at 25°C and 65% relative atmospheric humidity under 15000 lux. The growth in height is assessed 4 weeks after the application of the active substances.

The diminution produced by the active substance at various rates of application is indicated in the Table below in accordance with the following rating.

Key
6 = no action, as untreated grass
5 = approx. 16% inhibition of the growth in height
4 = approx. 35% inhibition of the growth in height
3 = approx. 50% inhibition of the growth in height
2 = approx. 66% inhibition of the growth in height
1 = approx. 85% inhibition of the growth in height
c = deeper leaf coloring Table III

| Active Substance Example No. | Concentration kg/ha | Lolium perenne | Poa pratensis | Festucca rubra | Festuca ovin |
| --- | --- | --- | --- | --- | --- |
| 1 | 10 | 5 | 3c | 6 | 6 |
|   | 5 | 5 | 6 | 6 | 6 |
| 2 | 10 | 4 | 1c | 4 | 3c |
|   | 5 | 5 | 2c | 5 | 3c |
| 3 | 10 | 5 | 4c | 5 | 4 |
|   | 5 | 6 | 4c | 5 | 4 |
| 4 | 10 | 2 | 3c | 4 | 3 |
|   | 5 | 4 | 3c | 4 | 4 | b. Application to cereals

Spring wheat, rye and oats are cultivated in seed dishes at 25°C, 65% relative atmospheric humidity and 15000 lux. When the plants have attained the 2 leaf stage the seed dishes are treated with an active substance broth, so that the indicated rate of application is achieved. The growth in length is assessed 21 days after application in accordance with the key in (a) above.

Table IV

| Active Substance Example No. | Concentration ppm | Spring Wheat | Rye | Oats |
| --- | --- | --- | --- | --- |
| 3 | 500 | 5 | 5 | 4 |
|   | 100 | 6 | 6 | 5 |
| 4 | 500 | 3 | 3 | 4 |
|   | 100 | 4 | 4 | 4 |

The same types of cereal, spring wheat, rye and oats, in the 2 leaf stage are sprayed dripping wet with aqueous or aqueous acetonic solutions of 0.5% active substance and then kept in a climatic chamber at 25°C and 65% relative atmospheric humidity under 15000 lux. The diminution in the growth in height of the plants is determined by measuring the internodal intervals.

The growth inhibition produced by the active substances is indicated in the following Table in accordance with the rating as given above.

Table V

| Active Substance Example No. | Concentration ppm | Spring Wheat | Rye | Oats |
| --- | --- | --- | --- | --- |
| 2 | 5000 | 4 | 3 | 3 |
|   | 1000 | 5 | 4 | 4 |
| 3 | 5000 | 3 | 3 | 3 |
|   | 1000 | 5 | 3 | 4 |

The other substances are tested in like manner and showed a similar action.

The herbicidal agents according to the invention are manufactured in known manner by intimately mixing and/or grinding active substances of the formula I with the suitable carriers, optionally with the addition of dispersants or solvents which are inert towards the active substances. The active substances may be available and can be used in the following forms:

Solid forms
  dusts, tracking agents, granules, coated granules, impregnated granules and homogeneous granules.

Liquid forms
  a. active substances which are dispersible in water: wettable powders, pastes, emulsions;
  b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used alone or in admixture with one another.

The particle size of the carriers for dusts is advantageously up to about 0.1 mm, for tracking agents about 0.075 to 0.2 mm, and for granules 0.2 mm or larger.

The concentrations of active substance in the solid preparations are usually from 0.5 to 80%.

To these mixtures can also be added additives which stabilize the active substance and/or non-ionic, anionic and cationic surface active substances, which for example improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulfonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, carrier, optionally additives which stabilize the active substance, surface-active substances and anti-foam agents and, optionally, solvents.

Wettable powders and pastes are obtained by mixing and grinding the active substances with dispersing agents and pulverulent carriers in suitable apparatus until homogeneity is attained. Carriers are, for example, those mentioned for the solid forms of application. In some cases it is advantageous to use mixtures of different carriers. As dispersing agents there can be used, for example, condensation products of sulfonated naphthalene and sulfonated naphthalene derivatives with formaldehyde, condensation products of naphthalene or naphthalene sulfonic acids with phenol and fomaldehyde, as well as alkali, ammonium and alkaline earth metal salts of lignin sulfonic acid, in addition, alkylaryl sulfonates, alkali and alkaline earth metal salts of dibutyl naphthalene sulfonic acid, fatty alcohol sulfates such as salts of sulfated hexadecanols, heptadecanols, octadecanols, and salts of sulfated fatty alcohol glycol ethers, the sodium salt of oleoyl ethionate, the sodium salt of oleoyl methyl tauride, ditertiary acetylene glycols, dialkyl dilauryl ammonium chloride and fatty acid alkali and alkaline earth metal salts.

Suitable anti-form agents are silicones.

The active substances are so mixed, ground, sieved and strained with the additives mentioned above that, in wettable powders, the solid particle size of from 0.02 to 0.04 and in pastes, of 0.03 is not exceeded. To produce emulsifiable concentrates and pastes, dispersing agents such as those given in the previous paragraphs, organic solvents and water are used. Examples of suitable solvents are the following: alcohols, benzene, xylenes, toluene, dimethyl sulfoxide, and mineral oil fractions boiling between 120° and 350°C. The solvents must be practically odorless, not phytotoxic, inert to the active substances and not readily inflammable.

Furthermore, the agents according to the invention can be applied in the form of solutions. For this purpose the active substance or several active substances of general formula I are dissolved in suitable organic solvents, mixtures of solvents or in water. Aliphatic and aromatic hydrocarbons, chlorinated derivatives thereof, alkyl naphthalenes, and mineral oils alone or mixed with each other, can be used as organic solvents. The solutions should contain the active substances in a concentration of from 1 to 20%.

The agents described according to the invention may be mixed with other biocidally active compounds or agents. Thus to broaden the activity spectrum the new agents may contain, for example, insecticides, fungicides, bactericides, fungistatics, bacteriostatics or nematocides, in addition to the cited compounds of the formula I.

Preparations forms of the new substituted azabicycloalkanes are described hereinbelow. Parts denote parts by weight.

Granules

The following substances are used to manufacture 5% granules:

5 parts of an active substance of the formula I,
0.25 parts of epichlorohydrin,
0.25 parts of cetyl polyglycol ether,
3.50 parts of polyethylene glycol ether (Carbowax),
91 parts of kaolin (particle size: 0.3-0.8 mm).

The active substance is mixed with epichlorohydrin and the mixture dissolved in 6 parts of acetone, then polyethylene glycol ether and cetyl polyglycol ether are added. The resulting solution is sprayed on kaolin and then evaporated in vacuo.

Wettable Powder

The following constituents are used to manufacture (a) a 70%, (b) a 25% and (c) a 10% wettable powder:

a. 70 parts of an active substance of the formula I,
5 parts of sodium dibutylnaphthalene sulphonate,
3 parts of napthalenesulphonic acid/phenolsulphonic acid/formaldehyde condensate (3:2:1),
10 parts of kaolin,
12 parts of Champagne chalk;

b. 25 parts of an active substance of the formula I,
5 parts of sodium oleylmethyltauride,
2.5 parts of naphthalenesulphonic acid/formaldehyde condensate,
0.5 parts of carboxymethyl cellulose,
5 parts of neutral potassium aluminium silicate,
62 parts of kaolin;

c. 10 parts of an active substance of the formula I,
3 parts of a mixture of the sodium salts of saturated fatty alcohol sulphates,
5 parts of naphthalenesulphonic acid/formaldehyde condensate,
82 parts of kaolin.

The indicated active substance is applied to the corresponding carriers (kaolin and chalk) and then these are mixed and ground, to yield wettable powders of excellent wettability and having an excellent capacity for forming suspensions. By diluting these wettable powders with water it is possible to obtain suspensions of every desired concentration of active substance. Such suspensions are used for combating weeds and weed-like grasses in cultures of water and dry rice before and after the emergence of the rice plants.

Paste

The following substances are used to manufacture a 45% paste:

45 parts of 1-(3-chloropropylthio-carbonyl)-cis-decahydroquinoline,
5 parts of sodium aluminium silicate,
14 parts of cetyl polyglycol ether with 8 mols of ethylene oxide,
1 parts of oleyl polyglycol ether with 5 mols of ethylene oxide,
2 parts of spindle oil,
10 parts of polyethylene glycol,
23 parts of water.

The active substance is intimately mixed with the additives in appropriate devices and ground. A paste is obtained from which, by diluting it with water, it is possible to manufacture suspensions of every desired concentration of active substance. The suspensions are suitable for treating cultures of water rice before and after the emergence of the plants.

Similar pastes are obtained if another active substance of the formula I is used instead of the above mentioned 1-(3-chloropropylthio-carboxnyl)-cis-decahydroquinoline.

Emulsion Concentrate

To manufacture a 10% emulsion concentrate
10 parts of 1-(allylthio-carbonyl)-trans-decahydroquinoline,
15 parts of oleyl polyglycol ether with 8 mols of ethylene oxide,
75 parts of isophoron are mixed together. This concentration can be diluted with water to give emulsions in desired concentrations. Such emulsions are applied, for example, to cultures of dry rice before the emergence of the rice plants.

Similar emulsion concentrates are obtained if, for example, 1-(allylthio-carbonyl)-2-methyl-decahydroquinoline or 1-(3-chloro-propylthio-carbonyl)-octahydroindole is used instead of the above mentioned active substance.

We claim:

1. A herbicidal composition which comprises (1) a herbicidally effective amount of a compound of the formula

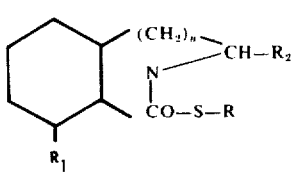

wherein R is chloroalkyl having 2 or 3 carbon atoms or a straight chain or branched alkenyl having 3 or 4 carbon atoms, one of $R_1$ and $R_2$ is hydrogen and the other is hydrogen or methyl, and $n$ is the number 1 or 2 and (2) an inert carrier.

2. A method for combating weeds which comprises applying to said plants a herbicidally effective amount of a compound of the formula

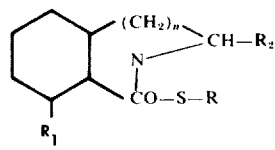

wherein R is chloroalkyl having 2 or 3 carbon atoms or a straight chain or branched alkenyl having 3 or 4 carbon atoms, one of $R_1$ and $R_2$ is hydrogen and the other is hydrogen or methyl, and $n$ is the number 1 or 2.

3. A method according to claim 2 in which $n$ is 2.

4. A method for controlling the growth of weeds in cultures of wheat, soya, cotton and maize which comprises applying thereto a herbicidally effective amount of a compound of the formula

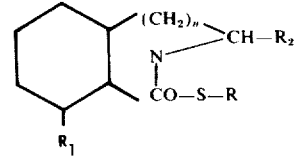

wherein R is chloroalkyl having 2 or 3 carbon atoms or a straight chain or branched alkenyl having 3 or 4 carbon atoms, one of $R_1$ and $R_2$ is hydrogen and the other is hydrogen or methyl, and $n$ is the number 1 or 2.

5. A method according to claim 4 in which $n$ is 2.

6. A method for controlling the growth of weeds in rice cultures which comprises applying thereto a herbicidally effective amount of a compound of the formula

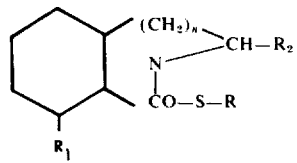

wherein R is chloroalkyl having 2 or 3 carbon atoms or a straight chain or branched alkenyl having 3 or 4 carbon atoms, one of $R_1$ and $R_2$ is hydrogen and the other is hydrogen or methyl, and $n$ is the number 1 or 2.

7. A method according to claim 6 in which $n$ is 2.

8. A method according to claim 7 in which the compound is 1-(allylthio-carbonyl)-trans-decahydroquinoline.

9. A method according to claim 7 in which the compound is 1-(3-n-chloropropylthio)-carbonyl)-cis-decahydroquinoline.

10. A method according to claim 7 in which the compound is 1-(3-n-chloropropylthio)-carbonyl)-trans-decahydroquinoline.

11. A method according to claim 7 in which the compound is 1-(allylthio-carbonyl)-cis-decahydroquinoline.

* * * * *